(12) United States Patent
Wallén

(10) Patent No.: US 8,491,563 B2
(45) Date of Patent: Jul. 23, 2013

(54) DEVICE FOR INJECTING MEDICAL SUBSTANCES

(75) Inventor: Claes Wallén, Sjömarken (SE)

(73) Assignee: Carmel Pharma AB, Gothenburg (SE)

( * ) Notice: Subject to any disclaimer, the term of this patent is extended or adjusted under 35 U.S.C. 154(b) by 443 days.

(21) Appl. No.: 10/520,724

(22) PCT Filed: Jul. 8, 2003

(86) PCT No.: PCT/SE03/01195
§ 371 (c)(1),
(2), (4) Date: Apr. 15, 2005

(87) PCT Pub. No.: WO2004/004823
PCT Pub. Date: Jan. 15, 2004

(65) Prior Publication Data
US 2005/0215976 A1 Sep. 29, 2005

Related U.S. Application Data

(60) Provisional application No. 60/394,289, filed on Jul. 9, 2002.

(30) Foreign Application Priority Data

Jul. 9, 2002 (SE) ..................................... 02021756

(51) Int. Cl.
*A61M 5/32* (2006.01)
(52) U.S. Cl.
USPC .......................................................... 604/411
(58) Field of Classification Search
USPC ................. 604/533, 537, 539, 282, 411, 403, 604/408, 414
See application file for complete search history.

(56) References Cited

U.S. PATENT DOCUMENTS

| | | | |
|---|---|---|---|
| 3,685,795 A * | 8/1972 | Caster ............................ | 251/342 |
| 3,986,508 A * | 10/1976 | Barrington ..................... | 604/411 |
| 4,412,834 A * | 11/1983 | Kulin et al. ..................... | 604/29 |
| 4,752,287 A * | 6/1988 | Kurtz et al. ................. | 604/99.02 |
| 5,122,123 A * | 6/1992 | Vaillancourt ................. | 604/192 |
| 5,158,554 A * | 10/1992 | Jepson et al. ................. | 604/539 |
| 5,201,725 A * | 4/1993 | Kling ............................ | 604/284 |
| 5,234,411 A * | 8/1993 | Vaillancourt ................. | 604/171 |

(Continued)

OTHER PUBLICATIONS

International Search Report dated Sep. 23, 2003.

*Primary Examiner* — Kevin C Sirmons
*Assistant Examiner* — Michael J Anderson
(74) *Attorney, Agent, or Firm* — Servilla Whitney LLC

(57) ABSTRACT

A device for injection, comprising a body (1) provided with a first channel (2) for conveyance of a first medical substance and a first connecting component (3) having a first port (4) for introduction of a first medical substance into said first channel (2), the connecting component (3) being connectable to an external unit, and a second channel (5) for conveyance of a second medical substance and a second connecting component (6) having a second port (7) which can be opened by means of an injection component for injecting a second medical substance into said second channel (5), and provided with a third connecting component (8) being common to the first and the second channels (2, 5) and having at least one third port (9) for conveying medical substances out from said first (2) and second (5) channels, the first (3), second (6) and third (8) connecting components and the body (1) being designed as an integrated unit.

13 Claims, 4 Drawing Sheets

U.S. PATENT DOCUMENTS

| | | | | |
|---|---|---|---|---|
| 5,254,097 A | * | 10/1993 | Schock et al. | 604/167.04 |
| 5,328,480 A | * | 7/1994 | Melker et al. | 604/164.11 |
| 5,470,522 A | | 11/1995 | Thome et al. | |
| 5,613,954 A | * | 3/1997 | Nelson et al. | 604/167.03 |
| 5,632,735 A | * | 5/1997 | Wyatt et al. | 604/539 |
| 5,685,866 A | * | 11/1997 | Lopez | 604/249 |
| 5,897,526 A | * | 4/1999 | Vaillancourt | 604/82 |
| 6,471,674 B1 | | 10/2002 | Emig et al. | |
| 2003/0191445 A1 | * | 10/2003 | Wallen et al. | 604/411 |

* cited by examiner

DEVICE FOR INJECTING MEDICAL SUBSTANCES

FIELD OF THE INVENTION AND PRIOR ART

The present invention relates to a device for injection, comprising a body provided with a first and a second channel for conveyance of medical substances, a first connecting component having a first port for introduction of a first medical substance into said first channel, a second connecting component having a second port for injecting a second medical substance into said second channel, and a third connecting component being common to the first and the second channels and having at least one third port for conveying medical substances out from said first and second channels.

The invention may be applied in different applications when medical substances are to be injected, but hereinafter the particular, but not limiting for the invention, fields of application concerning injection of medical substances, preferably liquids, where at the same time it is desired to transmit medical substances from two different sources to a receiving unit, such as for example a patient will be described for illuminating reasons.

Infusion bags are used for intravenous administration of liquid and medical effective substances to humans and animals. For this purpose, the infusion bag is provided with an outlet via which outlet fluid may flow to a component connected to the patient, such as a cannula or similar, and further into the body of the patient.

However, in certain cases there is a need for transmitting a second medical substance from a second source to the patient in a coordinated way, either at the same time as the intravenous administration of fluid or in connection to this administration, i.e. directly before and/or after this administration. To meet this need, up to now different system having several components in the form of connecting devices, which are assembled to one other and to flexible tubes, are used for accomplishing the desired transmissions of medical substances.

However, the prior art systems for parallel transmission of medical substances from different sources have disadvantages in that a non-insignificant work for assembling the components to each other for creating the systems is required, and the use of several components for achieving the system requires that a careful handling is observed to avoid contamination of the system and/or leakage of medical substances from the system to the environment.

THE OBJECT OF THE INVENTION AND SUMMARY OF THE INVENTION

One object of the invention is to provide a device of the kind defined by way of introduction for injection of medical substances, in which device at least some of the discussed disadvantages of such devices according to prior art are reduced to a substantial extent. This object is obtained by providing a device according to claim 1. By the fact that the first, second and third connecting component and the body are designed as an integrated unit the risk of leakage to the environment due to insufficient sealing between the connecting components and the body is eliminated. Furthermore, the risk of contamination of the medical substances and the components included is reduced since fewer separate components are to be handled for the preparation of the requisite equipment. A system including the device according to the invention may also potentially be rigged with fewer working operations and this in turn is time saving and cost effective.

According to a preferred embodiment of the invention said third connecting component constitutes a first coupling component provided with a thread for releasable connection to a second coupling component having a corresponding thread, for creating a coupling. In this way, using the device according to the invention and said second coupling component being arranged on for example a cannula which is inserted into the patient, the device according to the invention may be connected to the patient in a simple and reliable way so that medical substances from two different sources may be transmitted to the patient. By the provision of the thread joint a coupling which is save during tension load may be obtained at the same time as the connection of the device according to the invention and the other coupling component at the patient may be performed quickly and safely by few manipulations.

Further advantages and advantageous features of the device according to the invention are disclosed in the following description and remaining dependent claims.

The invention also relates to an injection arrangement according to claim 10.

BRIEF DESCRIPTION OF THE DRAWINGS

With reference to the appended drawings below follows a closer description of embodiments of the invention cited as examples.

In the drawings.

DETAILED DESCRIPTION OF PREFERRED EMBODIMENTS OF THE INVENTION

Figure 1:
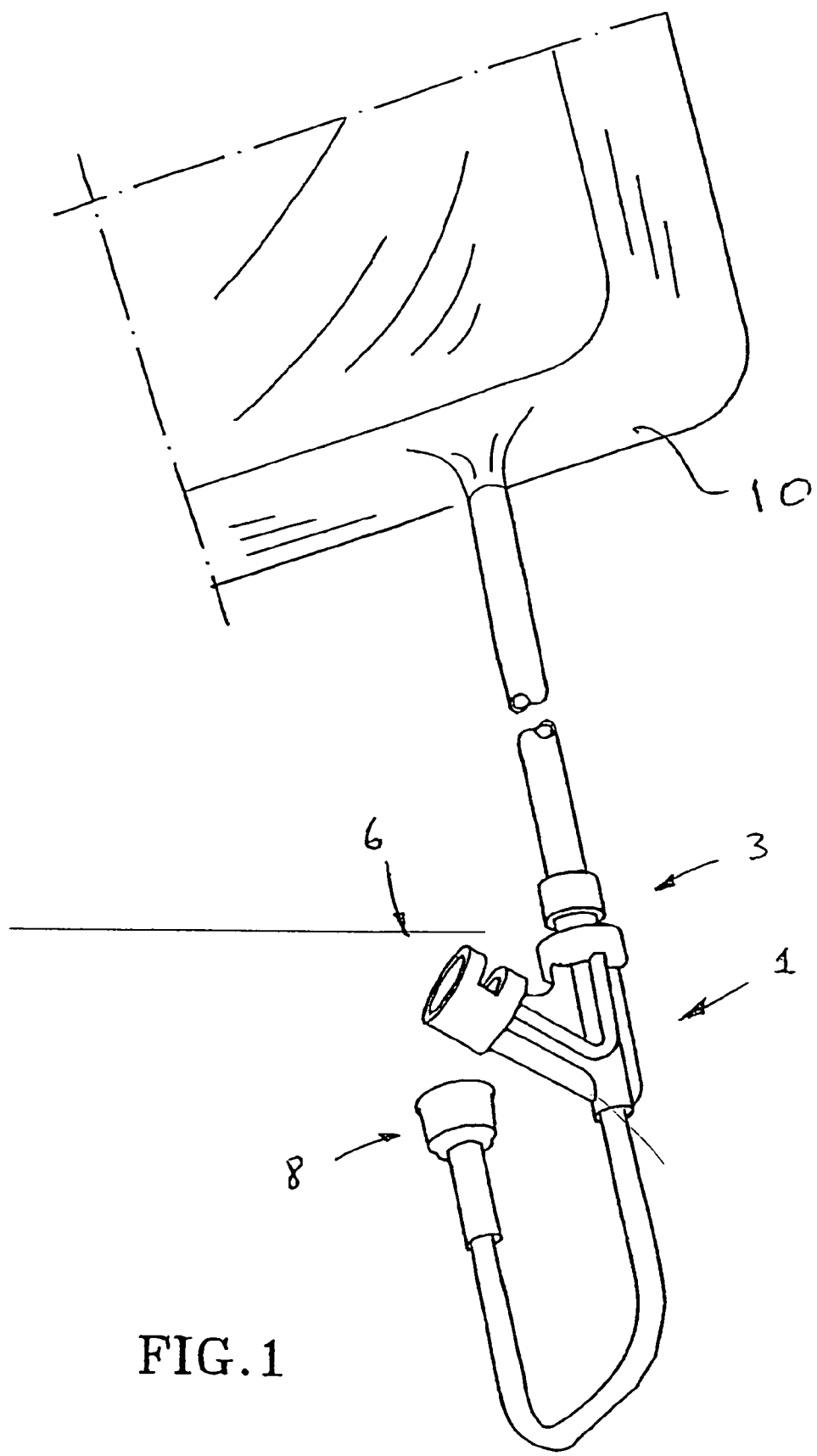
FIG. 1 is a perspective view of a device according to the invention together with an infusion bag.
Figure 2:
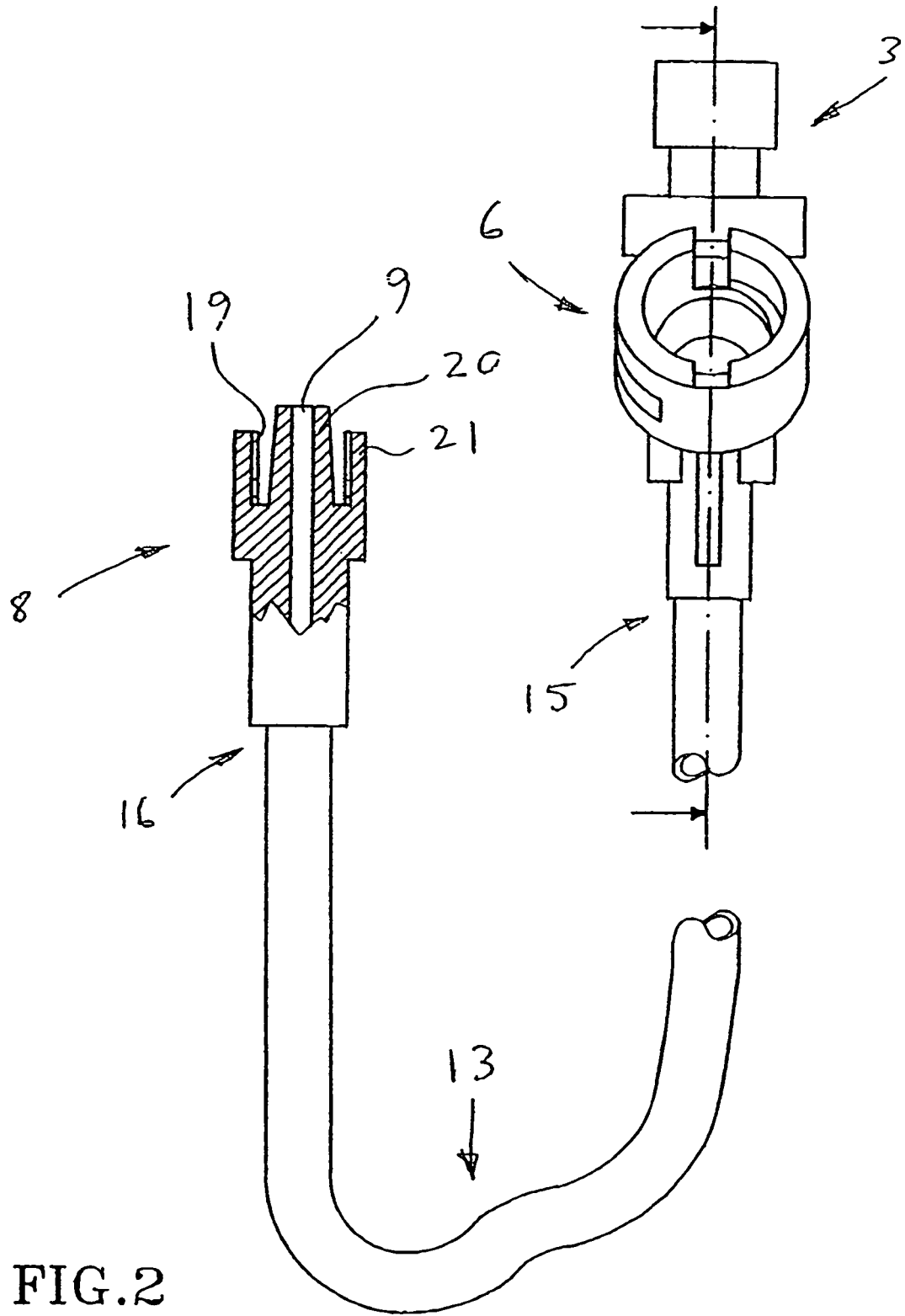
FIG. 2 is a view from above of the device according to the invention in FIG. 1.
Figure 2A:
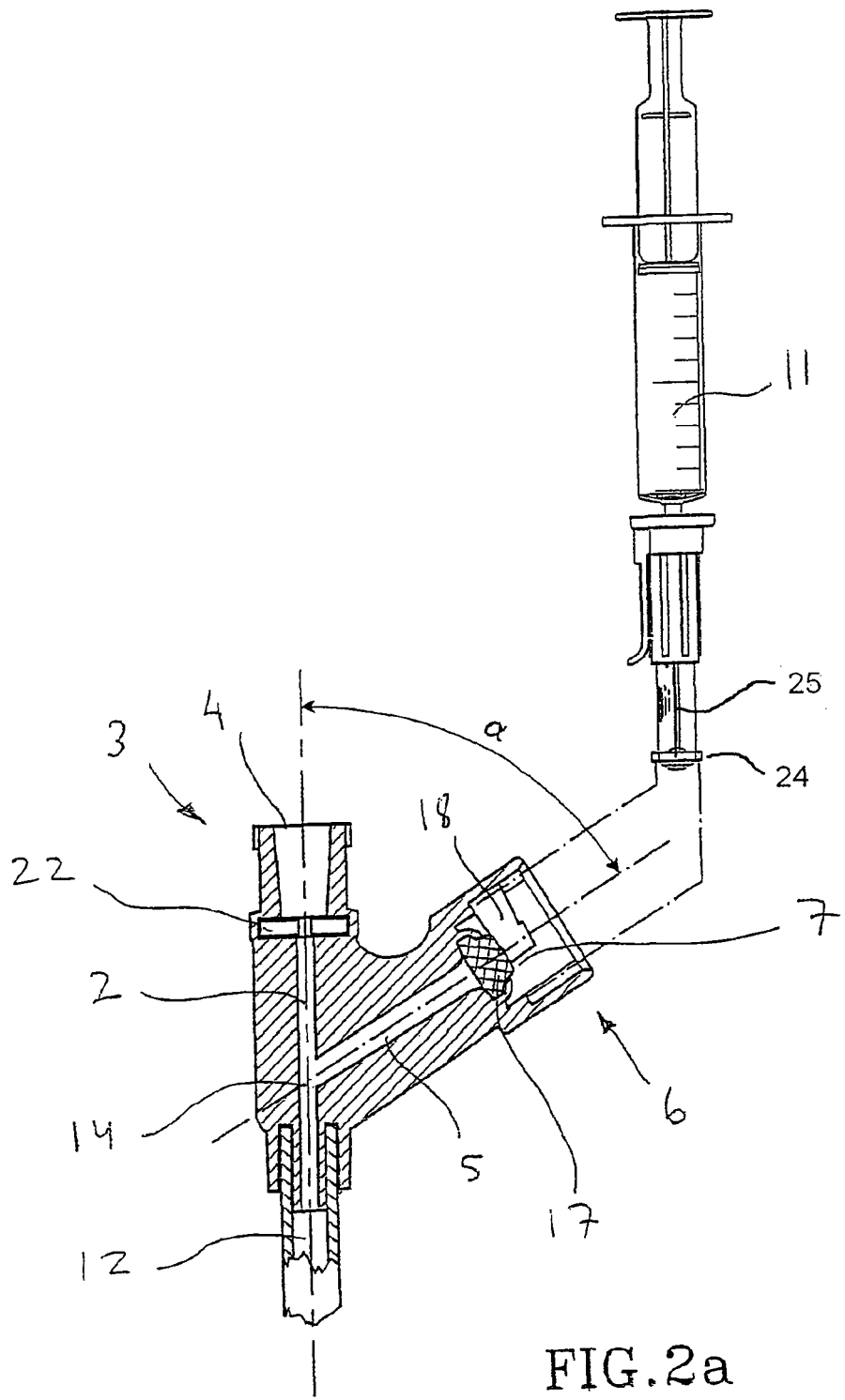
FIG. 2a is a cross-section view of the device according to the invention in FIG. 2 together with an injection component.

FIGS. 1, 2 and 2a illustrate a device according to the invention comprising a body 1 provided with a first channel 2 for conveyance of a first medical substance and a first connecting component 3 connectable to an external unit and having a first port 4 for introduction of a first medical substance into said first channel 2. Furthermore, the body 1 is provided with a second channel 5 for conveyance of a second medical substance and a second connecting component 6 having a second port 7, which can be opened by means of an injection component 11, for injecting a second medical substance into said second channel 5. In the other end, the body 1 is provided with a third connecting component 8 being common to the both channels 2, 5 and having at least one third port 9 for conveying medical substances out from said first 2 and second 5 channels. Said first 3, second 6 and third 8 connecting components and the body 1 are designed as an integrated unit. This means that these components 1, 3, 6, 8 are manufactured in one piece or joined to each other so that they form a connected unit being non-dismountable into the individual components.

The first channel 2 may be intended for conveyance of a medical substance from for example an infusion bag 10 to a patient and the second channel 5 may be intended for conveyance of a second medical substance, injected to the second channel 5 by means of for example a syringe 11, to the patient. Thus, the first 4 and second ports 7 are inlet ports of the body 1, whereas the third port 9 is an outlet port of the body 1.

Such as illustrated closer in FIGS. 2 and 2a the body 1 has a channel portion 12 common to the first and second channels and said third port 8 constitutes an outlet for this channel portion and thereby an outlet common to the first and second channels. In other words, the first 2 and the second channel 5 are arranged to lead into the channel portion 12 which is common to the channels and preferably the device is designed so that said second channel 5 constitutes a branch which connects to the first channel 2 in an oblique direction towards the first channel.

In the use of the device according to the invention it is often desired to place the first channel 2 vertically and the first connecting component 3 directed upwards so that fluid transportation, for example from an infusion bag 10 to a patient, is facilitated, whereas the second channel 5 suitably is arranged so that the length direction thereof forms an angle α, suitably in the interval 10-80°, and preferably in the interval 25-75°, relative to the length direction of the first channel 2. In the embodiment illustrated α is approximately equal to 60°. In this way conditions are created to suitably connect an injection component 11 to the second connecting component 6 and inject a substance in a direction towards the third port 9 for further transportation to a receiving unit such as a patient.

Although the device according to the invention, such as illustrated in FIGS. 1, 2 and 2a, advantageously has a body 1 provided with an elongated portion 13, for example a flexible tube which suitably is made of a relatively soft, flexible material such as plastic or similar, this portion 13 could be considerably shorter or be completely left out, which in such a case would imply that the third connecting component 8 would be arranged in the vicinity of the position 14 where the first and second channels meet.

However, the embodiment first mentioned has the advantage that when the third component 8 be connected to a compatible connecting component, for example arranged on a cannula which is introduced in a patient, this connection may be accomplished so that the main part of the device is located remote from the patient and so that affect on the cannula, and thereby on the patient, is avoided in the greatest possible extent. When using a flexible tube constituting said portion 13 the tube is suitably integrated with the remaining part of the device by that the both ends 15, 16 thereof being glued or welded to the body 1 and to the third connecting component 8, respectively. It should be pointed out that in a variant of the device according to the invention the first and the second channels could be arranged separated from each other, from respective inlet port up to the flexible tube, so that only the flexible tube portion of the body constitutes the channel portion which is common to the first and second channels.

The second connecting component 6 and the belonging second port 7 for injection of a second medical substance may be designed in different ways within the frame of the invention depending on which injection component 11 is desired to be connected. In the illustrated embodiment said second port 7, hereinafter denoted the injection port, has a first flexible membrane 17 for co-operation with a second flexible membrane 24 arranged in a injection component 11 which is connectable to said second connecting component 6. The first membrane 17 is suitable air- and liquid proof to provides for sealing of the injection port 7 when this is not used for injection. However, the injection port 7 may be opened by means of an injection component, for example by penetrating the membrane by means of an injection needle 25 for enabling injection when so is desired.

To achieve a sealed connection of such a injection component 11 to the second connecting component 6, i.e. to the injection port 7, the second connecting component 6 has a means 18 for holding said second flexible membrane 24 with a pressure against said first flexible membrane 17. This holding means 18 may for example be constituted by a snap lock device, bayonet coupling or similar. The current pressure is suitably chosen so that said first 17 and second 24 membranes are pressed together to a pressure exceeding the yield point of the both membranes, which implies that fluid cannot be pressed out through the contact surfaces of the membranes and a sealed connection is obtained.

If a pressure exceeding the yield point is applied the membranes will exhibits same properties at the compressed surfaces as in an arbitrary cross-section through the membranes, which implies that liquid cannot be pressed through the contact surfaces of the membrane. Such a characteristic may be obtained when said first and second membranes have been pressed together to a pressure exceeding 150 kPa. Since the device risks to be destroyed if it is subjected to exceedingly large contact forces, the contact pressure should be restricted as much as possible. It has been proved in experiments that a sufficient sealing without any risk of failure is obtained with contact forces up to 11.1 N, which corresponds to 565 kPa. Preferably, the contact pressure is within the interval 300-473 kPa.

The third connecting component 8 may advantageously be a first coupling component provided with a thread 19 for releasable connection to a second coupling component (not illustrated) having a corresponding thread, for creating a coupling. Such a connecting means in the form of a thread joint has the characteristic that said first and second coupling components are locked against rectilinear movements relative to each other when being connected to each other and the coupling is tension loaded. The first coupling component has a male fitting 20 and a ring 21 partly enclosing the male fitting, which ring exhibits said thread 19. The ring 21 is concentrically arranged relative to the male fitting 19. The second coupling component should comprise a female fitting provided with a further channel and an external thread corresponding to the thread 19 of the ring 21 and constituting part of the thread joint.

When the first and the second coupling components are to be connected to each other, i.e. when the first and second components be screwed together, the male fitting 20 be introduced into the female fitting to form a connection between the channel 12 of the first coupling component and the further channel of the second coupling component, which connection is sealed relative the environment. For this purpose the male fitting 20 and/or female fitting may be designed with a certain taper so that when the male fitting 20 and the female fitting have been brought together with a certain distance the outer surface of the male fitting will abut against the inner surface of the female fitting, and then further movement of the component in the introduction direction relative to each other is not longer possible and a sealing between the male fitting 20 and the female fitting is obtained when tightening the thread joint.

Although the first coupling component of the invention in the illustrated example is designed as a male fitting 20 in the coupling, in another embodiment it could be designed as a female fitting of the coupling, and the other coupling component, which is arranged on for example a cannula or some other component, could in such a case be designed as a corresponding male fitting. Of course it is also possible to change places of the threads in comparison to the illustrated embodiment, so that instead, the second coupling component including the female fitting is provided with an internal thread and the first coupling component including the male fitting is provided with an external thread. The threads may for example be arranged on rings such as described above.

Advantageously, the design of the threads 19, the male fitting 20 and the female fitting may be in accordance with a so called luer fitting coupling such as in the illustrated embodiment. Thus, preferably said third connecting component 8 is the male fitting of a luer fitting coupling.

The first connecting component 3 may for example constitute the male fitting or the female fitting in a luer fitting coupling and further the first connecting component 3 suitably comprises some kind of valve body 22, including for example a check valve, for regulating the flow in the first channel 2 and/or prevent fluid from being transported out from the body 1 via the first port 4.

Figure 3:
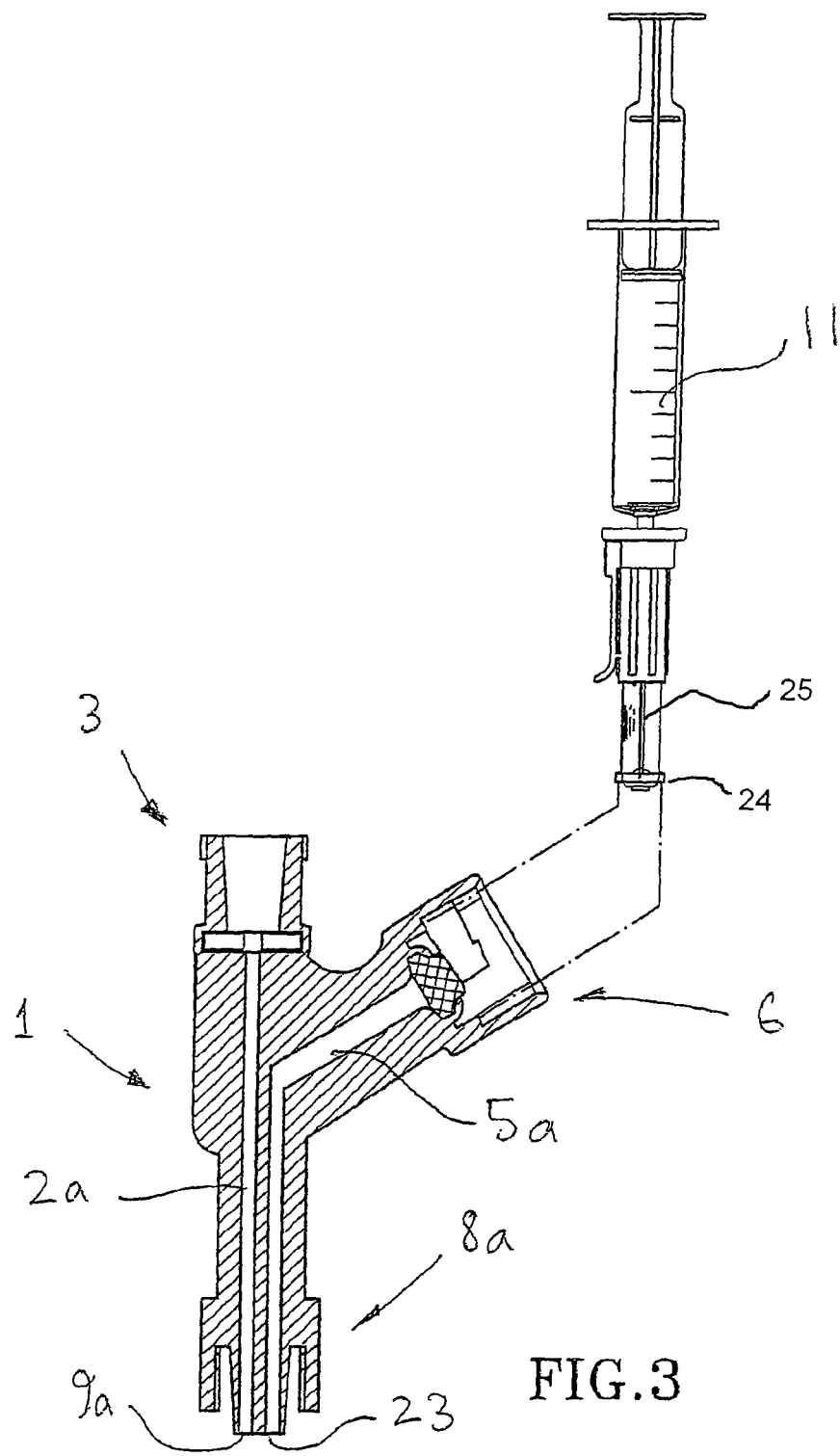
FIG. 3 is a cross-section view of a variant of the device according to invention.

In a variant of the device according to the invention illustrated in FIG. 3 said third connecting component 8a has a fourth port 23, wherein said third port 9a constitutes an outlet for the first channel 2a and said fourth port 23 constitutes and outlet for the second channel 5a. Thus, in this variant the both channels 2a, 5a are arranged separated from each other in the device and instead it is intended that both channels are brought together in an external component which is connected to the third connecting component 8a for transmitting a first and a second medical substance from two different sources to a receiving unit in common.

It is stressed that the invention is not limited to the exemplifying embodiments; rather within the scope of protection defined by the following claims, the invention may be varied in several ways once the idea of the invention is disclosed.

The invention claimed is:

1. A device for injection, comprising
a body comprising a first channel positioned and configured to convey a first medical substance;
a first connecting component comprising a first port for introduction of the first medical substance into said first channel, said first connecting component being configured and operative to connect to an elevated hanging fluid supply, wherein said first channel traverses the device in a generally straight vertical path when said first connecting component is connected to said elevated hanging fluid supply;
said body comprising a second channel positioned and configured to convey a second medical substance, said second channel forming an angle of between about 10 degrees and about 80 degrees with said first channel;
a second connecting component comprising a second port;
a first flexible air-proof and liquid-proof membrane positioned and configured to seal said second port, said first flexible membrane having no pre-existing openings therethrough, said first flexible membrane configured to be opened by an injection component operable for injecting the second medical substance into said second channel, said first flexible membrane being configured and operable to achieve a sealed connection with a second flexible air-proof and liquid-proof membrane having no pre-existing openings therethrough, the second flexible air-proof and liquid-proof membrane being arranged in said injection component which is connectable to said second connecting component;
said second connecting component having a holder configured and operative to hold said second flexible membrane with a pressure against said first flexible membrane; and
said body comprising a third connecting component in fluid communication with the first and the second channels, and said third connecting component comprising at least one third port positioned and configured as an outlet for the first channel and said third connecting component has a fourth port configured as an outlet for the second channel;
wherein said first, second and third connecting components and said body are an integrated unit, and wherein said first channel extends in a generally straight line through said body of said device.

2. A device according to claim 1, wherein said body has a separate channel portion for the first and the second channels, and said third port constitutes an outlet for said first channel portion.

3. A device according to claim 1, wherein said pressure exceeds 150 kPa.

4. A device according to claim 1, wherein said third connecting component comprises a first luer fitting component having a male fitting, configured to cooperate with a corresponding female fitting of a second luer fitting component, to thereby form a connection via said first and second luer fittings between said first and said second channels on one hand, and said second luer fitting component on the other hand, said connection being sealed relative to the environment.

5. A device according to claim 4, wherein said first luer fitting component comprises a ring which is concentrically arranged relative to said male fitting and at least partly encloses said male fitting, the ring being provided with said thread.

6. An injection arrangement comprising a device for injection according to claim 1;
a receiving unit connected to said third connecting component of the device for injection;
an infusion bag connected to said first connecting component of said device for injection,
the infusion bag containing a first medical substance in fluid communication with said receiving unit via said first channel; and
an injection component connected to said second connecting component of the device for injection, said injection component containing a second medical substance in fluid communication with said receiving unit via said second channel.

7. A device for injection, the device comprising:
a body comprising a first channel positioned and configured to convey a first medical substance;
a first connecting component comprising a first port for introduction of the first medical substance into said first channel, said connecting component being configured and operative to connect to an elevated hanging fluid supply, wherein said first channel traverses the device in a generally straight vertical path when said first connecting component is connected to said elevated hanging fluid supply;
a second channel positioned and configured to convey a second medical substance, said second channel forming an angle of between about 10 degrees and about 80 degrees with said first channel, said second channel having a proximal end;
a second connecting component comprising a second port,
a first flexible air-proof and liquid-proof membrane positioned and configured and operative to seal said second port, said first flexible air-proof and liquid-proof membrane having no pre-existing openings therethrough;
said first air-proof and liquid-proof membrane positioned at said proximal end of said second channel, and said second channel being configured and operative to be opened by an injection component for injecting a second medical substance into said second channel, said first flexible air-proof and liquid-proof membrane being operative to achieve a sealed connection with a second flexible membrane having no pre-existing openings therethrough, said second flexible membrane arranged in said injection component which is connectable to said second connecting component at the proximal end of the second channel;

said second connection component having a holder operative to hold said second flexible membrane with a pressure against said first flexible membrane; and a third connecting component in fluid communication with said first and second channels and having at least one third port configured as an outlet for the first channel and said third connecting component has a fourth port configured as an outlet for the second channel;

wherein said first, second and third connecting components and said body together comprise an integrated unit.

8. A device for injection, the device comprising:

a body comprising a first channel positioned and configured to convey a first medical substance;

a first connecting component comprising a first port for introduction of the first medical substance into said first channel, said connecting component configured and operative to connect to an elevated hanging fluid supply, wherein said first channel traverses the device in a generally straight vertical path when said first connecting component is connected to said elevated hanging fluid supply;

a second channel for conveyance of a second medical substance, said second channel forming an angle of between about 10 degrees and about 80 degrees with said first channel;

a second connecting component having a second port;

a first flexible air-proof and liquid-proof membrane configured and operative for sealing said second port, said first flexible air-proof and liquid-proof membrane lacking any pre-existing opening therethrough; and a third connecting component in fluid communication with said first and second channels, said third connecting component having a third port configured as an outlet for the first channel and said third connecting component has a fourth port configured as an outlet for the second channel;

wherein said first, second and third connecting components and said body together comprise an integrated unit;

an injection component configured and operative for injecting a second medical substance into said second channel, said injection component having a second flexible membrane with no pre-existing openings therethrough, and being configured and operative to be connected to said second connecting component; and said second connecting component having a holder configured and operative for holding said second flexible membrane with a pressure against said first flexible membrane.

9. A device for injection according to claim 1, wherein said injection component comprises an injection needle, and said first flexible membrane is configured and operative to be penetrated by said injection needle for said injecting said second medical substance.

10. A device for injection according to claim 8, wherein said injection component comprises an injection needle, and said first flexible membrane is configured and operative to be penetrated by said injection needle for the injection of said second medical substance.

11. A device for injection according to claim 1, wherein said hanging fluid supply is an infusion bag.

12. A device for injection according to claim 8, wherein said hanging fluid supply is an infusion bag.

13. A device for injection, the device comprising:

a body including a first channel for conveyance of a first medical substance, wherein the device is configured such that said first channel is oriented vertically in use;

a first connecting component with a first port configured for introduction of said first medical substance into said first channel under gravity;

a second channel for conveyance of a second medical substance, said second channel forming an angle of between about 10 degrees and about 80 degrees with said first channel, said second channel having a proximal end and a distal end, and being connected with said first channel at its distal end;

a second connecting component having a second port, a first flexible air-proof and liquid-proof membrane configured and operative for sealing said second port, said first flexible air-proof and liquid-proof membrane having no pre-existing openings therethrough;

said first air-proof and liquid-proof membrane positioned at said proximal end of said second channel, and said second channel being configured and operative to be opened by means of an injection component for injecting a second medical substance into said second channel, said first flexible air-proof and liquid-proof membrane being operative to achieve a sealed connection with a second flexible membrane having no pre-existing openings therethrough, said second flexible membrane arranged in said injection component which is connectable to said second connecting component at the proximal end of the second channel;

said second connection component having a holder operative for holding said second flexible membrane with a pressure against said first flexible membrane; and a third connecting component in fluid communication with said first and second channels and having at least one third port configured as an outlet for the first channel and said third connecting component has a fourth port configured as an outlet for the second channel;

wherein said first, second and third connecting components and said body together comprise an integrated unit.

* * * * *